(12) United States Patent
Alexis et al.

(10) Patent No.: US 10,694,976 B2
(45) Date of Patent: Jun. 30, 2020

(54) SQUEEZE PROTECTION

(71) Applicant: ELEKTA LTD., Crawley (GB)

(72) Inventors: Henrik Alexis, Vaxholm (SE); Kjell Eldered, Saltsjö-Duvnäs (SE); Erik Carlander, Stockholm (SE)

(73) Assignee: ELEKTA LTD., Crawley (GB)

( * ) Notice: Subject to any disclaimer, the term of this patent is extended or adjusted under 35 U.S.C. 154(b) by 511 days.

(21) Appl. No.: 15/586,988

(22) Filed: May 4, 2017

(65) Prior Publication Data

US 2018/0321337 A1    Nov. 8, 2018

(51) Int. Cl.
| | |
|---|---|
| *A61B 5/055* | (2006.01) |
| *A61B 6/04* | (2006.01) |
| *A61N 5/10* | (2006.01) |
| *A61N 5/00* | (2006.01) |

(52) U.S. Cl.
CPC .............. *A61B 5/0555* (2013.01); *A61N 5/10* (2013.01); *A61B 6/0407* (2013.01); *A61B 6/0442* (2013.01); *A61N 5/00* (2013.01); *A61N 2005/1097* (2013.01)

(58) Field of Classification Search
CPC ....... A61B 6/04; A61B 6/0407; A61B 6/0442; A61B 6/0457; A61B 5/0555; A61B 6/032; A61B 6/035
USPC .... 5/601, 600, 943; 378/209, 208, 205, 204, 378/20
See application file for complete search history.

(56) References Cited

U.S. PATENT DOCUMENTS

| | | | |
|---|---|---|---|
| 3,790,432 A | 2/1974 | Fletcher et al. | |
| 4,698,837 A * | 10/1987 | Van Steenburg | A61B 6/0442 378/208 |
| 4,956,885 A * | 9/1990 | Alich | A61B 6/0442 378/209 |
| 5,425,829 A | 6/1995 | Chang | |
| 5,771,513 A | 6/1998 | Kirchgeorg et al. | |
| 8,245,335 B2 * | 8/2012 | Shvartsberg | G01R 33/30 5/601 |
| 8,570,037 B2 * | 10/2013 | Schellekens | G01R 33/4812 324/309 |
| 9,081,067 B2 * | 7/2015 | Schellekens | G01R 33/3415 |
| 9,282,938 B2 * | 3/2016 | Aravamudan | A61B 6/0442 |
| 2010/0249575 A1 * | 9/2010 | Shvartsberg | G01R 33/30 600/415 |

(Continued)

FOREIGN PATENT DOCUMENTS

| | | | | |
|---|---|---|---|---|
| EP | 2141015 A2 | 1/2010 | | |
| EP | 3552544 A1 * | 10/2019 | ........... | A61B 5/0555 |

(Continued)

OTHER PUBLICATIONS

European Office Action, dated Jul. 4, 2019, for European Application No. 18168943.1.

(Continued)

*Primary Examiner* — Robert G Santos
(74) *Attorney, Agent, or Firm* — Birch, Stewart, Kolasch & Birch, LLP

(57) ABSTRACT

A structural element for use in a radiotherapy system or a magnetic resonance imaging system or a combination of a radiotherapy system and a magnetic resonance imaging system includes a plurality of fibers and a matrix, whereby the plurality of fibers are embedded in the matrix.

20 Claims, 6 Drawing Sheets

(56) References Cited

U.S. PATENT DOCUMENTS

| | | | | |
|---|---|---|---|---|
| 2011/0050226 A1* | 3/2011 | Schellekens | ......... | G01R 33/341 |
| | | | | 324/309 |
| 2012/0286786 A1* | 11/2012 | Schellekens | ....... | G01R 33/3415 |
| | | | | 324/322 |
| 2015/0327819 A1* | 11/2015 | Aravamudan | ......... | A61G 13/10 |
| | | | | 5/601 |
| 2018/0321337 A1* | 11/2018 | Alexis | .................. | A61B 5/0555 |

FOREIGN PATENT DOCUMENTS

| | | | |
|---|---|---|---|
| JP | | 2945703 B2 | 9/1999 |
| WO | WO 2010/111772 A1 | | 10/2010 |

OTHER PUBLICATIONS

Extended European Search Report, dated Sep. 17, 2018, for European Application No. 18168943.1.

* cited by examiner

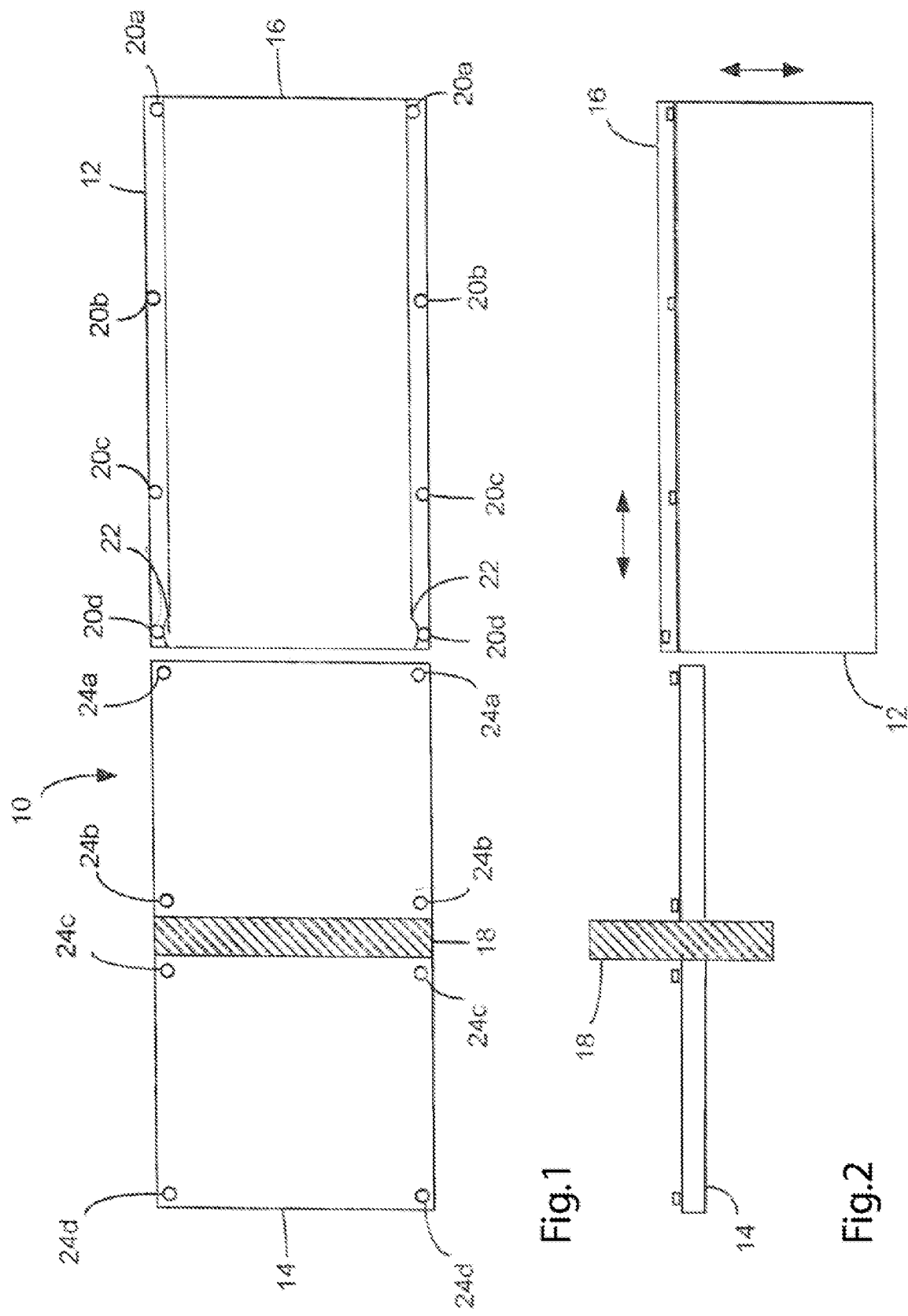

Fig.8a
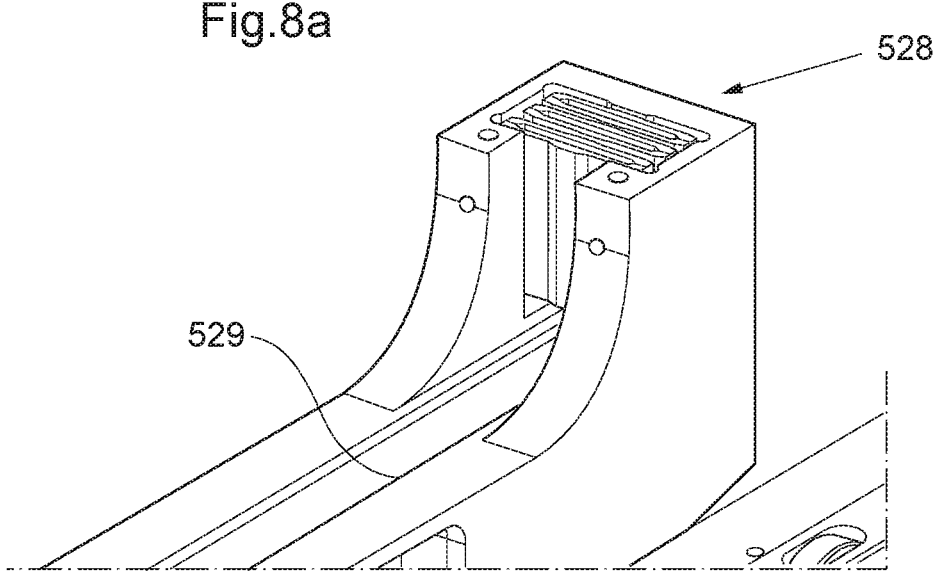
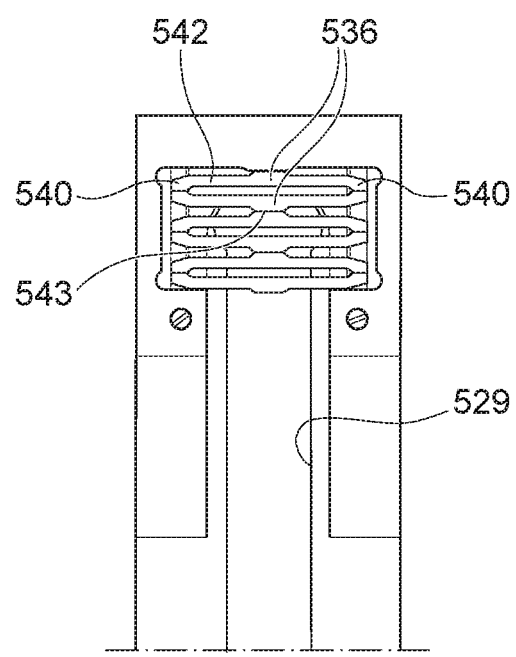
Fig.8b

SQUEEZE PROTECTION

TECHNICAL FIELD

The present invention relates to medical devices, and particularly to structural elements used in radiotherapy systems or magnetic resonance imaging systems or a combination of a radiotherapy system and a magnetic resonance imaging system.

BACKGROUND

In medical non-invasive therapy system in particular radiotherapy systems, such as conventional linear accelerators or MR Linac systems, the patient anatomy being treated or imaged should be aligned with the radiation isocentre as accurate as possible for each and every set up and each treatment fraction. One source of potential inaccuracy in the alignment is the repositioning of the bed on which the patient rests. As many medical radiotherapy systems require the patient to be placed into an enclosed and confined space, hereinafter called treatment bore, the patient must be set up for treatment outside the treatment bore and then transported into the treatment bore for the medical treatment to begin. Therefore, the bed must be movable between these two locations and positionable to a high degree of accuracy as misalignment during set up may entail that the patient will need to be removed from the medical radiotherapy system and realigned before treatment can commence, and thus wasting time and resources.

It is also of very high importance that the patient positioning is as stable as possible during the movement as well during the treatment or imaging. Hence, the position of the bed in treatment bore in the medical radiotherapy system must be very stable. The process of moving the bed from its support outside the medical radiotherapy system into the treatment bore inside the medical radiotherapy system itself requires careful alignment with the treatment table of the system as well as a high degree of stability.

Furthermore, it is also important that the patient set up and of moving the bed from its support outside the medical radiotherapy system into the treatment space inside the medical radiotherapy system is secure for the patient and easy to handle for the medical staff. The risk of patient injuries must be minimized during movement as well as during treatment in order to provide as high patient security as possible and minimize risk for patient movements during treatment.

Moreover, in medical non-invasive therapy systems, in particular in MR Linac systems, it is of very high importance that all material in the treatment bore or treatment volume is known and taken into account in the planning system. As all material will absorb radiation dose, it is important to reduce the material present in the treatment bore as much as possible and it is also important that the positions of material structures are known. In addition it is important to know the distribution of the material and further to ensure that the material does absorb as little magnetism and radiation as possible in order to provide good quality images with the magnetic resonance imaging system and to predict the dose of radiation that reaches the patient and the target tissue/position in or on the patient, respectively.

An additional requirement is that the material used for structural components and in particular for spring or elastic applications remains stable and keeps its characteristics even when exposed continuously to radiation. In particular plastic changes its characteristics when exposed to radiation over time; it gets brittle when exposed to radiation. The brittleness increases the risk of structural components breaking when exposed to deforming stress, which spring elements or other elastic elements usually are exposed to.

In summary, there is a number of important factors to take into account when designing structural elements for use in medical radiotherapy systems and/or magnetic resonance imaging systems or a combination of the two, such as MR Linac systems.

SUMMARY OF THE INVENTION

An object of the present invention is to provide a material that can be used to build structural elements and components in magnetic resonance imaging systems and radiotherapy systems without losing specific characteristics over time.

Another object is to provide a structural element in the form of spring elements or elastic mechanism that remain elastic even when exposed to radiation.

Another object is to provide a material that can be used to build structural elements in magnetic resonance imaging systems and radiotherapy systems, which material is easy to shape, is lightweight and durable even when exposed to magnetism and/or radiation.

A further object is to provide a material that does not have a tendency to creep even if it is exposed to a load over time in a radiation and/or magnetic resonance imaging environment.

This and other objects are fulfilled by the present invention as defined by the independent claims. Preferred embodiments are defined by the dependent claims.

According to an aspect of the present invention, there is provided a structural element for use in a radiotherapy system or a magnetic resonance imaging system or a combination of a radiotherapy system and a magnetic resonance imaging system. The structural element comprises a plurality of fibers and a matrix, whereby the plurality of fibers are embedded in the matrix.

Using fibers allows a designer to build structural components based on specific requirements. The fibers may allow the designer to design a structural element that is very rigid in one direction and flexible in another direction. This may for example be done by orientating the fibers accordingly in the matrix.

The plurality of fibers may be glass fibers or Kevlar fibers or a combination thereof. Kevlar fibers are para-aramid synthetic fibers.

Using glass fibers or Kevlar fibers may give the structural element strength, flexibility and elasticity. The glass or Kevlar fibers are not affected by radiation and they do not absorb magnetism or at least not in the same amount as metal does.

In an embodiment the matrix may comprise epoxy resin or polyester resin or a combination thereof.

In another embodiment the structural element may be an elastic structural element comprising a first elastic deformable element having a generally longitudinal shape, wherein the fibers embedded in the matrix are oriented parallel to the generally longitudinal shape.

By orientating the fibers along the longitudinal shape, the first elastic deformable element can be elastically bent around an axis perpendicular to the longitudinal shape, while in a direction parallel to the longitudinal shape the first elastic deformable element remains rigid and resistant.

The direction of the longitudinal shape of the first elastic deformable element may change along the length of the first elastic deformable element. Thus the first elastic deformable element may for instance be generally S-shaped, C-shaped, L-shaped or a combination thereof while the orientation of the fibers may be parallel to the S-shape, C-shape or L-shape or the combination thereof. In other words, the fibers are oriented parallel to the longitudinal shape at any point in the first elastic deformable element.

In a further embodiment the structural element may comprise a second element being connected to the first elastic deformable element, the second element having a generally longitudinal shape extending at least more or less parallel to the generally longitudinal shape of the first of the first elastic deformable element. The second element may further comprise a first longitudinal lateral side extending at least more or less parallel to the generally longitudinal shape of the second element, whereby the first longitudinal lateral side is configured to be arranged above a guide rail, for example of a movable patient bed, in order to elastically close a gap created by the guide rail.

Such a structural element may for example by used when covering guide tracks or gaps of the non-invasive medical therapy system, such as for example guide tracks of a movable patient bed or the like. The second element may be configured to elastically close access to the guide rail or track or the like so that the patient cannot put a limb in the guide track when the patient bed is moved into and out of the treatment bore. This reduces the risk of the patient squeezing a finger or other limb.

The first longitudinal lateral side of the second element may preferably be straight.

In an embodiment the elastic deformable element may be connected to the second element on a second longitudinal lateral side being arranged opposite the first longitudinal lateral side.

In another embodiment the second element may be at least partially U-shaped and the first elastic deformable element may be rod-shaped, wherein each one of free ends of the rod-shaped first elastic deformable element engages a respective leg of the U-shaped second element.

The rod-shaped first elastic deformable element may be configured to be connected to the U-shaped second element via holes in each of the respective legs of the U-shape. Alternatively the rod-shaped first elastic deformable element may be integrally connected to the legs of the U-shaped second element.

In embodiments the first elastic deformable element may be integrally formed with the second element.

In another embodiment the first elastic deformable element may comprise a free end whereby the first elastic deformable element may be configured to interact with a part of a radiotherapy system and/or a magnetic resonance imaging system. The interaction may be done via the free end or alternatively via any part of the elastic structural element, the first elastic element or the second element.

The free end may for example be connected, for example so it can rotate freely, to another structural component of the radiotherapy system and/or a magnetic resonance system via the free end.

The other structural component can be a guide track or any other gap that requires a flexible cover. Such a gap may for instance be gap through which liquid can penetrate into areas such liquid is not wanted.

Alternatively the free end may be configured to push or abut against another structural component of the radiotherapy system and/or a magnetic resonance system via the free end. In the above examples such a connection or abutment may lead to the first elastic deformable element being abler to elastically flex when pushed towards- or pulled away from the connection or abutment. Thus the first elastic deformable element may be used in a similar manner as an elastic spring.

Alternatively to the above described, the second element may be configured to be connected to another structural component of the radiotherapy system and/or a magnetic resonance system. In such an embodiment the first elastic deformable element may be configured to elastically close access to a guide track or the like.

In another embodiment the first elastic deformable element may comprise a shoulder part having and an arm part having a free end, said shoulder part and arm part being integrally formed and wherein the shoulder part is connected integrally to a second longitudinal lateral side of the second element opposite the first longitudinal lateral side and wherein the free end of the arm part may be configured to interact with a part of the radiation therapy system and/or the magnetic resonance imaging system.

In another embodiment the first elastic deformable element comprises a first and a second shoulder part, a first and second arm part and a first and second free end, wherein in between the first free and the second free end the first and second shoulder parts and the first and second arm parts are alternatively and integrally formed with each other form an elastically compressible spring element.

In an embodiment the at least two elastic deformable elements are connected to each other via the shoulder parts in a zigzag manner. The zigzag shape may be an S-shape comprising several S integrally formed with each other.

In an alternative embodiment to the above, the arm parts each comprise a protrusion and two shoulder parts and wherein the at least two first elastic deformable elements are connected to each other via the shoulder parts forming an O-shape and wherein the at least two first elastic deformable elements are oriented so that the protrusions are arranged on an outer side of the O-shape.

By providing one or several of these O-shapes a spring element can be provided.

Such a compressible elastic spring element may be used as an end stop for example for the patient bed so that the stop of the patient bed does not take place immediately and abruptly but is rather smooth and comfortable for the patient.

Another embodiment disclosed herein is the use of a material comprising fibers embedded in matrix as a structural component in non-invasive medical therapy systems.

The fibers may comprise glass fibers or Kevlar fibers or a combination thereof.

The matrix may comprise epoxy resin or polyester or a combination thereof.

As mentioned previously the above material may have improved properties for withstanding radiation over time and also a minimal influence on a magnetic field such as in a magnetic resonance imaging system. The material even be used in computer tomography systems.

The non-invasive medical therapy system may be a radiotherapy system or a magnetic resonance imaging system or a combination of a magnetic resonance imaging and a radiotherapy system.

In an embodiment the structural component may be an elastic structural element or a spring element.

Disclosed herein is further a system for elastically closing a gap of a guide rail in a radiotherapy system and/or a magnetic resonance imaging system. The system may comprise at least two elastic structural elements according to any of the above described embodiments, whereby the two elastic structural elements are arranged so that the first longitudinal lateral sides face each other and are in contact with each other above the gap.

The longitudinal lateral sides may be elastically moved apart when the patient bed is moved into or out of the treatment bore in order to make space for a support that connects the patient bed with the guide rail.

Such a system protects the patient and reduces the risk of squeezing a limb anywhere between the guide rail, patient bed or support.

BRIEF DESCRIPTION OF THE DRAWINGS

For a better understanding of the present invention, and to show more clearly how it may be carried into effect, reference will now be made, by way of example, to the following drawings, in which:

FIG. 1 shows a plan view of a system according to embodiments of the present invention;

FIG. 2 shows a side view of the system according to embodiments of the present invention;

FIG. 8a illustrates a spring element according to the invention similar to the one illustrated in FIG. 6;

FIG. 8b illustrates top down view onto the spring element of FIG. 8a;

FIG. 9b illustrates a perspective view of the elastic structural element shown in FIG. 9a.

DESCRIPTION

Figure 3A:
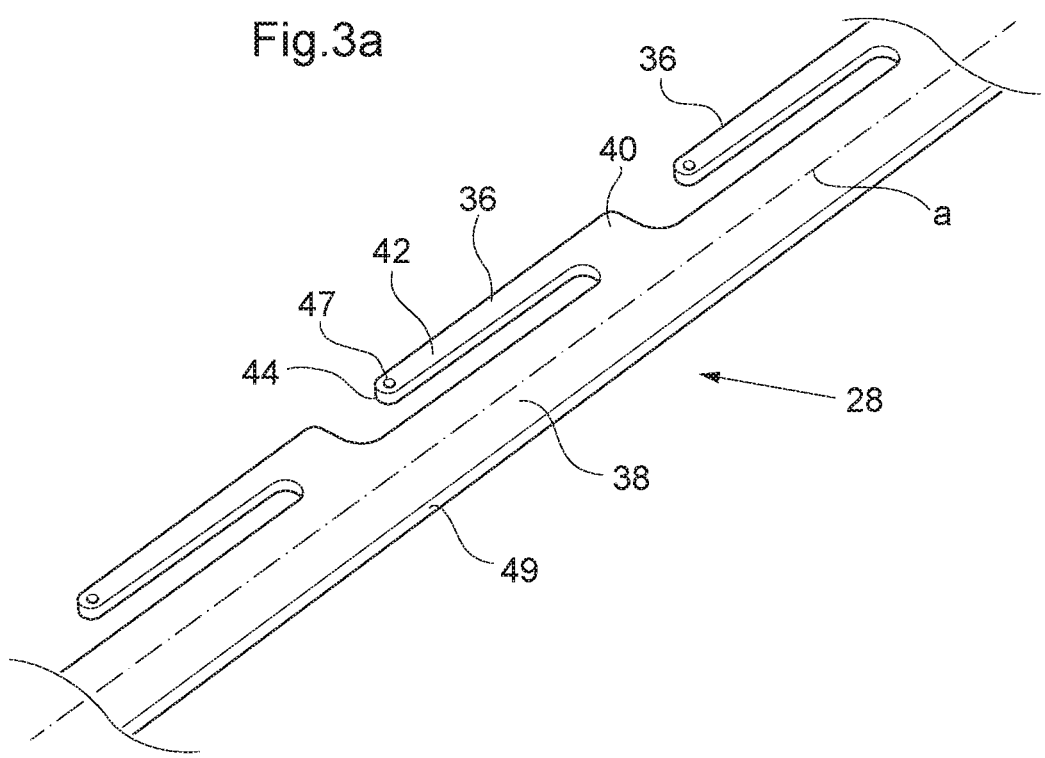
FIG. 3a shows a perspective view of an elastic structural element according to embodiments of the present invention.

FIG. 1 shows a plan view of a system 10 according to embodiments of the present invention and FIG. 2 shows a side view of the system of FIG. 1. The system 10 comprises a patient support 12, a treatment table 14, and a bed 16 which is movable between the patient support 12 and the treatment table 14. The treatment table 16 is schematically shown in FIGS. 1 and 2 and may form part of any medical treatment system but is particularly suitable for use in MR Linac radiotherapy systems. Hence, in embodiments of the present invention, the system 10 is arranged at a MR Linac radiotherapy system having radiation heads and radiation sources for generating beams of therapeutic radiation emanating from the radiation heads. One or more collimating elements (e.g. a Multi-leaf collimator in the Linac part) are provided for shaping the beam to conform to a desired cross-section. The radiation heads may be mounted on a rotatable gantry, and controlled to rotate around the patient while directing the radiation towards the axis of rotation and the target within the patient. The target thus receives radiation from multiple angles and a higher dose than the surrounding healthy tissue. The extent of the treatment area 18, i.e. the volume in which the radiation beam operates, is illustrated schematically in FIGS. 1 and 2.

The patient support 12 may comprise a mechanism for altering the height of the support, for example, between a first height and second height. For example, the first (lower) height may be at a level suitable to allow the patient to climb on to the bed 16, while the second (higher) height is a level equal to the height of the treatment table 14 and allows the bed 16 to move between the support 12 and the treatment table 14.

The bed 16 may be moved in a direction along its longitudinal axis between the support 12 and the treatment table 14 in a manner to be described in more detail below. Those skilled in the art will appreciate that any suitable mechanism may be used for moving the bed 16. For example, the bed 16 may be moved by a pulley/belt system, a rack and pinion system, a conveyor belt, etc.

As described above, it is important that the bed can be smoothly transferred or moved between the support 12 and the treatment table 14 so that once on the table 14 the bed is correctly aligned within the system, which in many radiotherapy systems is crucial. In order to ensure that the bed 16 is correctly aligned during initial set-up and treatment, the system 10 may comprise guide elements 20a, 20b, 20c, 20d, arranged on an upper surface of the support 12. Alternatively, guide tracks may be arranged on an upper surface of the support 12 and treatment table 14 and corresponding guide rails may be arranged on the patient bed 16 such that the bed 16 can slide seamlessly between the support and the table.

In the illustrated embodiment, the patient support comprises four pairs of guide elements. However, fewer or more guide pairs may be provided without departing from the scope of the invention. The guide pairs may be uniformly spaced, along the edges of the support 12 so as to prevent the bed 16 from moving significantly in the lateral direction (i.e. up and down the page in FIG. 1, or into and out of the page in FIG. 2).

In the embodiment illustrated in FIGS. 1 and 2, the guide elements are rollers which move over the edge of the bed 16 as the bed moved in the direction along its longitudinal axis. However, those skilled in the art will appreciate that any suitable guiding element which provides a low friction surface along which the bed can travel without sticking may be provided as an alternative. Further, guides need not be identical, and a mix of different guides may be provided in the same system without departing from the scope of the invention. The patient bed 16 may for example move on guide tracks (not shown) or the like.

The treatment table 14 may comprise a plurality of guide elements 24a, 24b, 24c, 24d, on an upper surface of the table, similar to the guide elements on the support 12. The guide elements 24a, 24b, 24c, 24d may further be used together with guide tracks as mentioned above.

The patient bed 16 may further be configured to engage stop elements (not shown in FIGS. 1 and 2) when reaching its position in the treatment area 18 and when it is moved backed in the position outside of the treatment area 18.

The guide tracks need to be covered with an elastic system in order to avoid injury of the patient. It may for instance be possible to put a limb in particular a hand or finger in the guide track upon which movement of the patient bed 16 this limb or finger may be sheared off. Thus there is a need to provide a safe system that covers such guide tracks but still allows a support element (not shown), which supports the patient bed 16 to move and elastically push away the elements of the elastic system. Other guide tracks or movement tracks may be foreseen in the system 10, which other guide tracks or movement tracks may also require covering. The below explained embodiment is thus not limited to particular guide tracks but more general to any application within the system 10 requiring the covering of a guide track or gap. Mechanisms and embodiments for covering tracks are explained referring to FIGS. 3a to 5.

Figure 7:
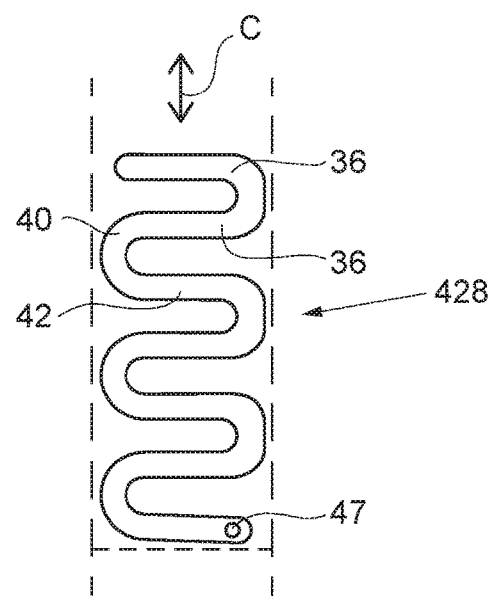
FIG. 7; shows a top down view on a spring element according to the invention.

The stop elements may preferably be elastic bumpers in order to provide a smooth and comfortable experience to the patient and to avoid any injury by stopping the movement of the patient bed 16 abruptly. Stop elements may also be used for other applications in the system 10 such other applications are course be covered herewith. Embodiments of a stop element in the form of a spring element is shown in FIGS. 7 to 8b.

Figure 3B:
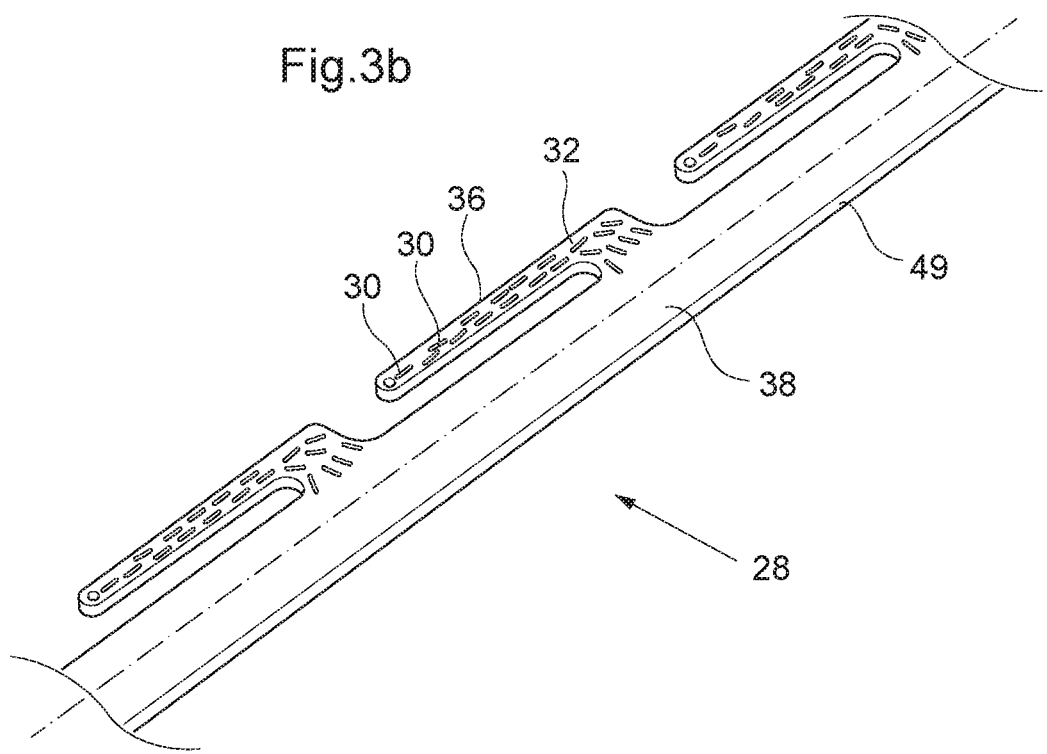
FIG. 3b shows a similar perspective view of the elastic structural element as FIG. 3a indicating a fiber orientation.

Referring to FIGS. 3a and 3b embodiments of an elastic structural element 28 is now described. The elastic structural element 28 is made of fibers 30 embedded in a matrix 32 as partially shown in FIG. 3b. The fibers 30 may be glass fibers or Kevlar fibers or a mixture thereof. The matrix 32 may be an epoxy resin or a polyester resin or a mixture thereof.

Figure 4:
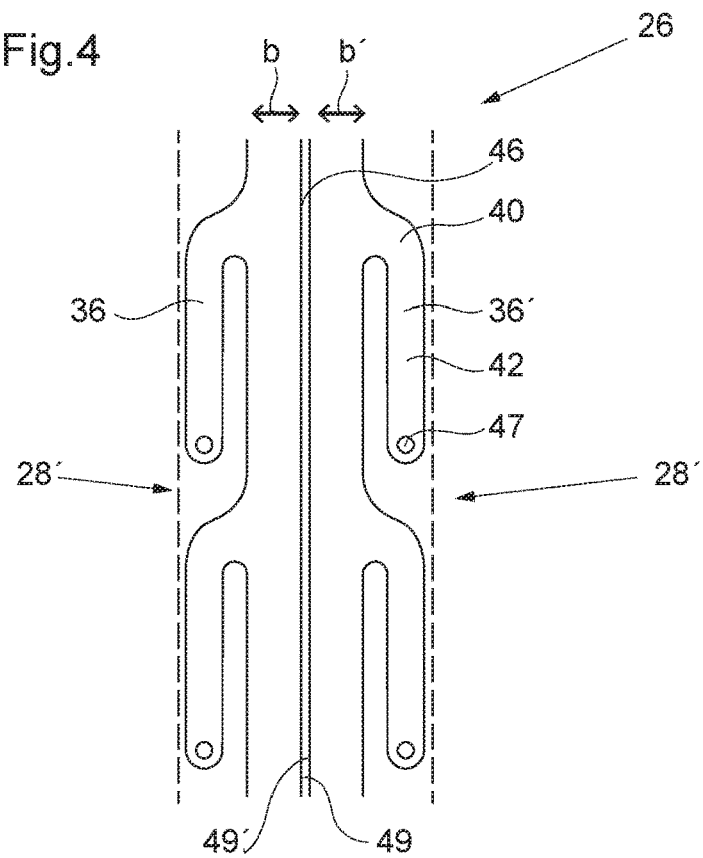
FIG. 4 shows a top down view onto two elastic structural elements as illustrated in FIGS. 3a and 3b forming an elastic system.

The elastic structural element 28 comprises a first elastic deformable element 36 and a second element 38. The first elastic deformable element 36 is integrally formed with the second element 38. As can be seen in FIGS. 3a and 3b each second element 38 may comprise one or more first elastic deformable elements 36. The first elastic deformable element 36 each comprise a shoulder part 40 and an arm part 42. The arm part 42 comprises a free end 44. The shoulder part 40 is integrally formed with the second element 38 and connected to a longitudinal lateral side thereof. The arm part 42 in combination with the shoulder part 40 allows the first elastic deformable element 36 to flex and elastically move transverse to a longitudinal direction a of the second element 38. This is also illustrated in FIG. 4, which will be explained later herein. In FIG. 3a the free end 44 is provided with a recess 47, for example for engaging a screw or the like for connecting the structural element 28 to another structural element or part of the system 10 of FIGS. 1 and 2.

Figure 5:
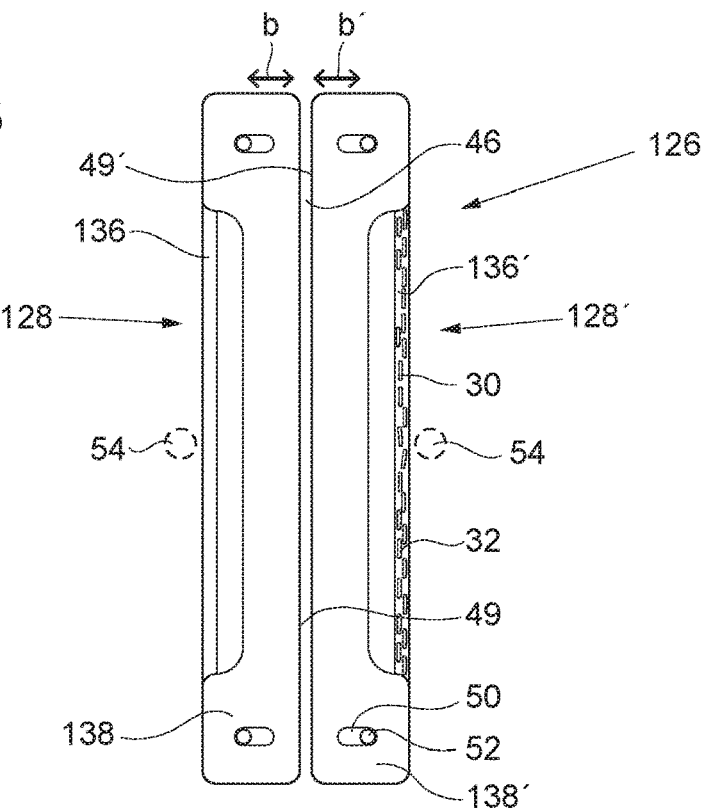
FIG. 5 shows a top down view of another embodiment of an elastic system according to the invention.

FIGS. 3a-6 further also illustrate a first longitudinal lateral side 49, 49' of the second element 38, 38', 138, 138', 238. This first longitudinal lateral side 49, 49' is preferably straight and may be used to cover a gap 46 (c.f. FIGS. 4 and 5). The gap 46 may provide access to a guide rail for a patient bed. Opposite the first longitudinal lateral side 49, 49' a second longitudinal lateral side may be arranged to which second longitudinal lateral side the first elastic deformable elements 36, 36', 136, 136', 236 may be connected.

Now referring in particular to FIG. 3b a fiber 30 orientation is further explained. Since the first elastic deformable element 36 is designed to be deformable the fibers 30 are oriented parallel to a longitudinal shape of the first elastic deformable element 36 at any point thereof. Thus even if the first elastic deformable element 36 is not a straight element but rather comprises also the shoulder part 40 as shown, the fibers 30 generally follow the curve of the shoulder part 40 as illustrated in FIG. 3b. In other word the fibers 30 are oriented following the general, current longitudinal direction or shape of the first elastic element 36 at any point thereof. The fiber orientation is not illustrated in the second element 28, since this second element 28 can be designed rigid and non-elastic deformable thus the fibers 30 can theoretically be oriented randomly or crosswise. The matrix 32, in which the fibers 30 are embedded, is also schematically indicated in FIG. 3b. The fibers 30 may not be visible they are indicated for understanding and illustrative purposes.

The general shape of the structural element 28, 128, 228 is further not designed to have any sharp edges or sharp corners to avoid tension peaks during deformation. Tension peaks could lead to a destruction of the structural element 28, 128, 228 and they should be avoided.

Turning now to FIG. 4, the function of an elastic system 26 comprising a first and second elastic structural element 28, 28' is herewith explained. The arrows b, b' indicate how the gap 46 may open for instance when a support of the patient bed 16 is travelling through it. When the gap 46 opens the first flexible elements 36, 36' may elastically deform due to their design and allow the support the patient bed 16 to pass through the gap 46. Once such a support or the like has passed the first elastic deformable elements 36, 36' will move back into their original position and thereby close the gap 46 again.

The elastic structural elements 28, 28' may be connected to another structural element of the system 10, for example a guide track or the like, via the recesses 47 and screws (not shown). The connection may be done using a sleeve or the like (not shown) to ensure that the arm part 42 can freely rotate while still being connected to the other structural component and the guide track, respectively.

Alternatively to the above described screw and recess connection the arm part 42 may abut against a wall or the like of the guide track. The wall of the guide track is illustrated in dashed lines in FIG. 4. The abutment at this wall or similar may be enough to motivate the first elastic deformable element 36, 36' to elastically deform when the second element 38 is pushed towards the wall when the support of the patient bed 16 is for instance moving through the gap 48.

FIG. 5 illustrates a similar elastic system 126 as FIG. 4 but with a different design of the structural elements 128, 128'. The arrows b, b' illustrate the elastic movement of the structural elements 128, 128' upon a support moving through the gap 46. The elastic deformation in this case is provided by first elastic deformable elements 136, 136'. The first elastic deformable elements 136, 136' are shaped in the form of rods, for example produced by pultruding, while the fibers 30 in the matrix 32 are oriented in a longitudinal direction of the rod. The second elements 138, 138' may again be provided as rather rigid elements made of fibers embedded in a matrix, whereby the fibers may be randomly oriented. The second element(s) 138, 138' has a longitudinal shape and is generally U-shaped whereby the two legs of the U-shape are perpendicularly oriented to the longitudinal shape, as illustrated in FIG. 5. The first elastic deformable elements 136, 136' may be form fitted into the second elements 138, 138' or glued to the second elements 138, 138', engaging the two legs of the U-shape, respectively. Form fitted may mean that the free ends of the rods may engage in recesses (not shown) provided in the second elements 138, 138'. Each second element 138, 138' may comprise one or more rods as first elastic deformable elements 136, 136' as previously described.

In order to allow an elastic deformation the second elements 138, 138' may comprise fixing means in the form of an elongated recesses 50, in which recesses a pin 52 or screw or the like may engage, whereby said pin or screw may for example be connected to a guide track of the system 10. The fixing means or connection means may further comprise an additional pin 54 or screw, which additional pin or screw may be configured to engage the first elastic deformable element 136, 136' when the second elements 138, 138' are pushed away from the gap 48. The additional pin 54 is illustrated in dashed lines in FIG. 5.

Even though the elastic system of FIGS. 4 and 5 has been shown comprising a pair of elastic structural elements 28, 28', 128, 128' it is clear that one elastic structural element 28, 28', 128, 128' may be enough to protect a guide track or gap. The structural element may example abut one longitudinal side of the guide track.

In FIGS. 4 and 5 a pair of elastic structural elements 28, 28', 128, 128' are illustrated for covering the gap 46 via the first longitudinal lateral side 49, 49'. It is however possible to cover the gap 46 with only one single elastic structural element 28, 128, 228.

Figure 6:
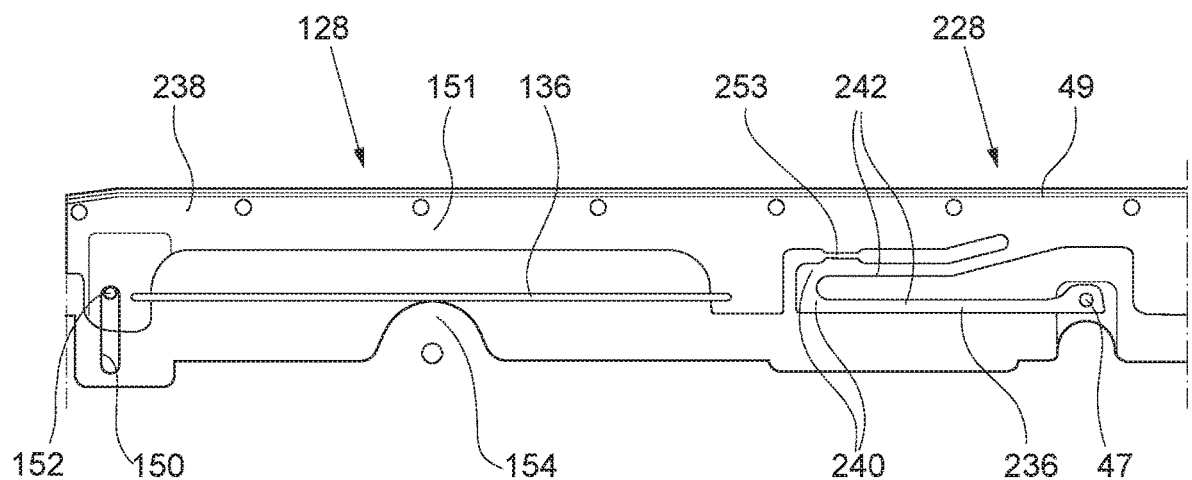
FIG. 6 shows a top down view onto a combination of the structural elements according to the invention shown in FIGS. 4 and 5

FIG. 6 illustrates one side of an elastic system comprising a combination of a structural element 228 similar to the one shown in FIGS. 3 to 4 and another structural element 128 similar to the one shown in FIG. 5. From FIG. 6 it can be seen that the elastic structural element 128 comprising the rod shaped first elastic deformable element 136 is positioned at a beginning of a squeeze or guide rail protection whereby further inwards a structural element 28 as illustrated in FIGS. 3 to 4 is used. The elongated recess 150 and pin 150 are also illustrated in FIG. 6. The pin 54 as shown in FIG. 5 is illustrated as an extension 154 in FIG. 6, which extension may for example by part of a guide track or the like. A plate 151, made of a similar fiber and matrix material or other material, may be arranged above the elastic system in order to minimize risk of squeezing for the patient. The plate 151 may thus cover the first elastic element(s) 136, 236 and the second element 238. In FIG. 6 the second element 238 may be seen as the entire rigid element extending over the first elastic element in rod-shaped 136 and the first elastic element 236 similarly shaped to the one illustrated in FIGS. 3 to 4. The first elastic element 236 may be shaped in an S-shape comprising two arm parts 242 and two shoulder parts 240. At least one of the arm parts 242 may be partially oblique relative to a longitudinal extension of the elastic system, whereby the oblique part may be integrally formed with the second element 238. The first elastic element 236 shown in FIG. 6 may further comprise a protrusion 253 or the like to limit certain movements, when the first elastic deformable element 236 is flexing.

The elastic system 26, 126, 226 has now been described by illustrating several embodiments. Any other embodiments or combinations of the two embodiments fall herewith within the scope of the invention. Further the first elastic deformable elements 36, 36', 136, 136, 236 and/or the second elements 38, 38', 138, 138', 238 may at least partially be sandwiched between one or two plates 151 or the like so that only a small longitudinal section of the second elements 38, 38', 138, 138', 238 close to the gap 48 is free. Such plates 151 may for example ensure that the patient cannot put her or his fingers anywhere close the elastically movable parts, such as the arm and should parts 42, 242, 40 240. The recess 47 is also illustrated in FIG. 6, showing that the elastic system 226 can be connected to the guide track or the like via the recess.

FIG. 7 illustrates an elastic system or a structural element 428 that comprises a plurality of first elastic deformable elements 36 but no second elements. This structural element 428 may be a spring element which can be used as a stop at the end of a guide track or the like. The spring element 428 is built up by connecting several first elastic deformable elements 36 via their shoulder parts 40 and arm parts 42, respectively, in zigzag manner. The spring element 428 thus looks like several S-shaped elements interconnected with one another. The first elastic deformable elements 36 may be integrally formed with one another whereby the orientation of the fibers (not shown in FIG. 5) follows the S-shape or zigzag shape of the spring element 428. This design allows the spring element 428 to elastically deform in a direction indicated by the arrow c. When the spring element 428 is thus positioned in a guide track, which is indicated in dashed lines in FIG. 7, it can slowly and progressively stop any element or support that runs in the guide track by deforming along the arrow c. As soon as the pressure from such a moving element or support is released the spring element 428 will elastically move back into its original, non-deformed position as shown in FIG. 7.

The spring element 428 may be connected to the guide track or the like via the recess 47 and a pin or screw as previously described. Alternatively it may abut a wall on one side as indicated in FIG. 7 with a dashed line close to the recess 47.

FIGS. 8a and 8b illustrate a similar elastic stop element as FIG. 7, whereby FIG. 8a illustrates a perspective view and FIG. 8b a top down view. As mentioned the stop element or spring element 528 may be arranged at the end or beginning of a guide track 529, for example a guide track 529 for the patient bed 16. The spring element 528 may comprise first elastic deformable elements 536 comprising an arm part 542, whereby each arm part 542 comprises a shoulder part 540 at its free ends. The shoulder parts 540 of two first elastic deformable elements 536 may abut one another so that the two first elastic deformable elements 536 form an O-shaped shape. Each arm part 542 may comprise a protrusion 543 which is arranged in the same place for all arm parts 542 so that the protrusions 543 abut one another thereby distancing each O-shape from each other and allowing the spring element 528 to be deformed and compressed.

Figure 9A:
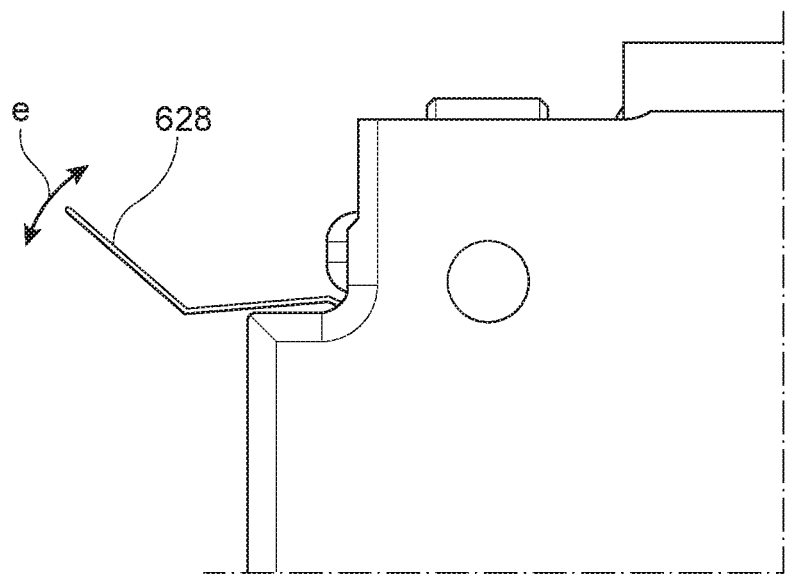
FIG. 9a illustrates a side view of another elastic structural element according the invention.
Figure 9B:
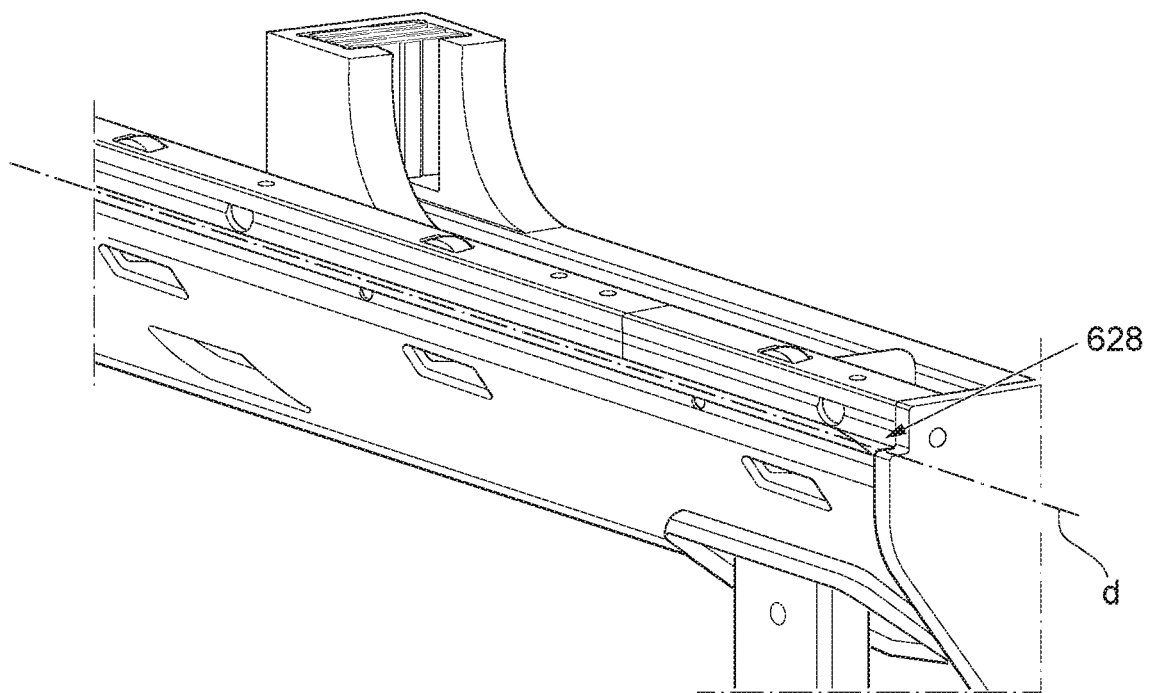

FIGS. 9a and 9b further illustrate another embodiment relating to the use of an elastic structural element 628 according to the invention. The elastic structural element 628 works as a protection for liquids so that the liquids cannot flow into a gap in between the treatment volume 18 and the treatment table 14. In FIG. 9b a longitudinal direction D of the elastic structural element 628 is indicated. In this case the fibers are oriented perpendicular to the longitudinal direction so that the elastic structural element 628 can elastically deform around an axis defined by the longitudinal direction d. This deformation is indicated by the arrow c in FIG. 9a.

Although the structural element has now been described using an elastically deformable system as shown in FIGS. 3a to 9b, it is clear that the structural elements and components made of glass—and or Kevlar fibers embedded in an epoxy resin or polyester resin matrix may be used for other applications in radiotherapy environments or magnetic resonance imaging system environments due to their specific material properties and characteristics. An advantage can for instance be that due to their flexibility when it comes to designing various shapes, the shapes of the structural components/elements can be adapted and changed depending for example on test results and measurements, to suit specific engineering requirements.

The invention claimed is:

1. A structural element for use in a radiotherapy system or a magnetic resonance imaging system or a combination of a radiotherapy system and a magnetic resonance imaging system, the structural element comprising:
   a plurality of fibers; and
   a matrix,
   wherein the plurality of fibers are embedded in the matrix, and
   wherein said structural element is an elastic structural element arranged to cover or to protect a guide track, a guide rail or a gap of a patient bed or a treatment table in the radiotherapy system or the magnetic resonance imaging system or the combination of the radiotherapy system and the magnetic resonance imaging system.

2. The structural element according to claim 1, wherein the plurality of fibers are glass fibers or fibers sold under the trademark of Kevlar or a combination thereof.

3. The structural element according to claim 2, wherein the matrix comprises epoxy resin or polyester resin or a combination thereof.

4. The structural element according to claim 1, wherein the matrix comprises epoxy resin or polyester resin or a combination thereof.

5. The structural element according to claim 1, wherein the structural element comprises a first elastic deformable element-having a generally longitudinal shape, wherein the fibers embedded in the matrix are oriented parallel to the generally longitudinal shape.

6. The structural element according to claim 5, comprising a second element being connected to the first elastic deformable element, the second element having a generally longitudinal shape extending in parallel to the generally longitudinal shape of the first elastic deformable element, wherein the second element comprises a first longitudinal lateral side extending in parallel to the generally longitudinal shape of the second element, said first longitudinal lateral side being configured to be arranged above the guide rail in order to elastically close a gap of the guide rail.

7. The structural element according to claim 6, wherein the first elastic deformable element is connected to the second element on an opposite side of the longitudinal lateral side.

8. The structural element according to claim 7, wherein the second element is at least partially U-shaped and wherein the first elastic deformable element is rod-shaped, wherein each one of free ends of the rod-shaped first elastic deformable element engages a respective leg of the U-shaped second element.

9. A system for elastically closing a gap of a guide rail in a radiotherapy system and/or a magnetic resonance imaging system comprising at least two elastic structural elements according to claim 7, wherein the two elastic structural elements are arranged so that the first longitudinal sides face each other and are in contact with each other above the gap.

10. The structural element according to claim 6, wherein the second element is at least partially U-shaped and wherein the first elastic deformable element is rod-shaped, wherein each one of free ends of the rod-shaped first elastic deformable element engages a respective leg of the U-shaped second element.

11. The structural element according to claim 6, wherein the first elastic deformable element is integrally formed with the second element.

12. The structural element according to claim 11, wherein the first elastic deformable element comprises an arm part with a free end and wherein the first elastic deformable element is configured to interact with a part of a radiotherapy system and/or a magnetic resonance imaging system via the free end.

13. The structural element according to claim 12, wherein the first elastic deformable element comprises a shoulder part and the arm part having a free end, said shoulder part and arm part being integrally formed with one another, whereby the shoulder part is integrally connected to a second longitudinal lateral side of the second element opposite the first longitudinal lateral side, and wherein the free end of the arm part is configured to interact with a part of the radiotherapy system and/or the magnetic resonance imaging system.

14. A system for elastically closing a gap of a guide rail in a radiotherapy system and/or a magnetic resonance imaging system comprising at least two elastic structural elements according to claim 6, wherein the two elastic structural elements are arranged so that the first longitudinal sides face each other and are in contact with each other above the gap.

15. The structural element according to claim 5, comprising at least two first elastic deformable elements each having a shoulder part and an arm part, wherein arm parts of one first elastic deformable element are connected to shoulder parts of another first elastic deformable element in order to form an elastically deformable spring element.

16. Use of a material comprising fibers embedded in matrix as a structural element in a system including a patient support, a treatment table and a patient bed, wherein said structural element is an elastic structural element arranged to cover or protect a guide track or gap of the patient bed or the treatment table.

17. The use of the material of claim 16, wherein the fibers comprise of glass fibers or Kevlar fibers sold under the trademark of Kevlar or a combination thereof.

18. The use of the material according to claim 17, wherein the matrix comprises epoxy resin or polyester resin or a combination thereof.

19. The use of the material according to claim 16, wherein the matrix comprises epoxy resin or polyester resin or a combination thereof.

20. The use of the material according to claim 16, wherein the system is a radiotherapy system or a magnetic resonance imaging system or a combination of a magnetic resonance imaging and a radiotherapy system.

* * * * *